United States Patent [19]

Gorton et al.

[11] Patent Number: 5,051,536

[45] Date of Patent: Sep. 24, 1991

[54] METHOD FOR ISOMERIZING 1,2-DICHLOROETHENE

[75] Inventors: Earl M. Gorton, Sulphur; John D. Driskill; Randall M. Hall, both of Lake Charles, all of La.

[73] Assignee: PPG Industries, Inc., Pittsburgh, Pa.

[21] Appl. No.: 435,098

[22] Filed: Nov. 13, 1989

Related U.S. Application Data

[63] Continuation-in-part of Ser. No. 211,617, Jun. 27, 1988, abandoned.

[51] Int. Cl.$^5$ .................... C07C 17/00; C07C 21/073
[52] U.S. Cl. .................... 570/236; 570/202; 570/216
[58] Field of Search ............... 570/202, 235, 236, 256, 570/216

[56] References Cited

U.S. PATENT DOCUMENTS

| | | | |
|---|---|---|---|
| 3,435,081 | 3/1969 | Wilks et al. | 570/236 |
| 3,515,760 | 6/1970 | Wild | 570/236 |
| 3,560,579 | 2/1971 | Bacha et al. | 570/202 |
| 3,584,065 | 6/1971 | Oshima | 570/236 |
| 3,751,493 | 8/1973 | Cappa et al. | 570/236 |
| 3,836,592 | 9/1974 | Gordon | 570/236 |
| 3,914,167 | 10/1975 | Ivy et al. | 570/236 |
| 4,409,407 | 10/1983 | Petruck et al. | 570/236 |
| 4,781,807 | 11/1988 | Clark, Jr. et al. | 570/236 |

FOREIGN PATENT DOCUMENTS 0270006  6/1988  European Pat. Off. ............ 570/236

OTHER PUBLICATIONS

Kirk-Othmer, Encyclopedia of Chemical Technology, 2nd Ed., vol. 5, pp. 178–183 (1964).
Kirk-Othmer, Encyclopedia of Chemical Technology, 3rd Ed., vol. 5, pp. 742–745 (1979).

*Primary Examiner*—Werren B. Lone
*Attorney, Agent, or Firm*—George D. Morris

[57] ABSTRACT

One stereoisomer of 1,2-dichloroethene is isomerized to the other stereoisomer in the liquid phase and in the presence of free radical initiator.

56 Claims, No Drawings

METHOD FOR ISOMERIZING 1,2-DICHLOROETHENE

CROSS-REFERENCE TO RELATED APPLICATION

This application is a continuation-in-part of application Ser. No. 211,617, filed June 27, 1988, now abandoned.

BACKGROUND OF THE INVENTION

Both trans-1,2-dichloroethene [CAS 156-60-5] and cis-1,2-dichloroethene [CAS 156-59-2] are valuable compounds having a variety of uses. They may be used separately or together in various proportions as low temperature extraction solvents for heat sensitive substances, as solvent for the manufacture of rubber solutions, and as coolant in refrigeration plants. Each compound has been copolymerized with other ethylenically unsaturated monomers to form copolymers.

1,2-Dichlororethene [CAS 540-59-0] can be produced by direct chlorination of acetylene at about 40° C. to about 80° C., by the reduction of 1,1,2,2-tetrachloroethane, by the pyrolytic dehydrochlorination of 1,1,2-trichloroethane, or as a by-product in the chlorination of chlorinated compounds. However produced, the 1,2-dichloroethene comprises a mixture of the trans and cis isomers, the proportions of which depend upon the conditions of manufacture.

For some uses, trans-1,2-dichloroethene or a trans-rich mixture of the two stereoisomers is preferred. Trans-1,2-dichloroethene is more reactive chemically than the cis-isomer, especially in 1,2-addition reactions. It also has a lower normal boiling point and a lower latent heat of vaporization than the cis-isomer, thereby favoring the trans-isomer or a trans-rich mixture for extractions where it is desired to recover the 1,2-dichloroethene by distillation for recycle. The trans-isomer also has a lower viscosity than the cis-isomer, so that less energy is required for pumping the trans-isomer or trans-rich mixture of the two stereoisomers.

For other uses, cis-1,2-dichloroethene or a cis-rich mixture of the two stereoisomers is preferred. Since the cis-isomer has a lower melting point than the trans-isomer, the cis-isomer or a cis-rich mixture is better suited for use as an indirect heat transfer medium in refrigeration systems operating at low temperatures. The solubility of the cis-isomer in water at 25° C. is less than that of the trans-isomer, so that the cis-isomer or a cis-rich mixture of the stereoisomers is preferred for some extractions where an aqueous phase is present. The lower chemical activity of the cis-isomer is advantageous where chemical stability is desired.

It is therefore desirable in many instances to isomerize cis-1,2-dichloroethene to trans-1,2-dichloroethen or vice versa, depending upon the intended use of the product.

Processes are known for effectuating the isomerization. In the presence of bromine or alumina at high temperatures, one isomer can be partially converted to the other. The direction of the reaction depends upon the relative concentrations of the isomer in the reaction mixture as compared with the equilibrium concentrations at the conditions of pressure and temperature prevailing during the reaction. At 825° C., for example, the equilibrium mixture contains about 55 percent of the cis-isomer, while at 975° C. the proportion of the cis-isomer falls to 52 percent.

THE INVENTION

It has now been found that isomerization can be promoted in the liquid phase at relatively low temperatures when the reaction is conducted in the presence of free radical initiator.

Accordingly, the invention is a method comprising isomerizing one stereoisomer of 1,2-dichloroethene to the other stereoisomer of 1,2-dichloroethene in the liquid phase and in the presence of free radical initiator.

A preferred embodiment is a method comprising isomerizing cis-1,2-dichloroethene to trans-1,2-dichloroethene in the liquid phase and in the presence of free radical initiator.

The same free radical initiators can be used to promote the liquid phase isomerization of trans-1,2-dichloroethene to cis-1,2-dichloroethene. Another embodiment, therefore, is a method comprising isomerizing trans-1,2-dichloroethene to cis-1,2-dichloroethene in the liquid phase and in the presence of free radical initiator.

It is expected that the direction of the liquid phase reaction depends upon the relative concentrations of the isomers in the reaction mixture as compared with the equilibrium concentrations at the temperature conditions prevailing during the reaction.

The free radical initiators which can be used in the present invention are many and widely varied. In most cases, organic free radical initiators are used.

One class of suitable organic free radical initiators comprises the organic peroxygen-containing free radical initiators. This class may be divided into a large number of subclasses, some of which are as follows:

Peroxides, exemplified by diethyl peroxide, di-tert-butyl peroxide [CAS 110-05-4], n-butyl 4,4-bis(tert-butylperoxy)valerate, 1,1-bis(tert-butylperoxy)-3,3,5-trimethylcyclohexane, bis-tert-butyl peroxides of diisopropylbenzene, dicumyl peroxide [CAS-80-43-3], 2,5-dimethyl-2,5-bis(tert-butylperoxy)hexane [CAS 78-63-7], and 2,5-dimethyl-2,5-bis(tert-butylperoxy)-3-hexyne [CAS 1068-27-5].

Hydroperoxides exemplified by methyl hydroperoxide, tert-butyl hydroperoxide [CAS 75-91-2], cumyl hydroperoxide [CAS 80-15-9], 2,5-dimethyl-2,5-dihydroperoxyhexane [CAS 3025-88-5], p-menthanehydroperoxide [CAS 80-47-7], and diisopropylbenzene hydroperoxide [CAS 98-49-7].

Ketone peroxides, exemplified by methyl ethyl ketone peroxide, methyl isobutyl ketone peroxide, cyclohexanone peroxide, 2,4-pentanedione peroxide, the 1,2,4,5-tetraoxacyclohexanes, and the 1,2,4,5,7,8-hexaoxacyclononanes.

Aldehyde peroxides, exemplified by bis(1-hydroxyheptyl) peroxide.

Diperoxyketals, exemplified by 2,2-bis(tert-butylperoxy)butane [CAS 2167-23-9], ethyl 3,3-bis(tert-butylperoxy)butyrate [CAS 55794-20-2], 1,1-bis(tert-butylperoxy)cyclohexane [CAS 3006-86-8], and 1,1-bis(tert-butylperoxy)-3,3,5-trimethylcyclohexane [CAS 6731-36-8].

Diacyl peroxides, exemplified by diacetyl peroxide [CAS 110-22-5], dibenzoyl peroxide [CAS 94-36-0], dicaprylyl peroxide, bis(4-chlorobenzoyl) peroxide, didecanoyl peroxide, bis(2,4-dichlorobenzoyl) peroxide [CAS 133-14-2], diisobutyryl peroxide [CAS 3437-84-1], diisononanoyl peroxide, dilauroyl peroxide [CAS 105-74-8], dipelargonyl peroxide, dipropionyl peroxide, and bis(3-carboxylpropionyl) peroxide.

Peroxycarboxylic acids, exemplified by peroxyacetic acid.

Peroxyesters, exemplified by tert-butyl peroxyacetate [CAS 107-71-1], methyl peroxyacetate, tert-butyl peroxybenzoate [CAS 614-45-9] tert-butyl peroxy(2-ethylhexanonate) [CAS 3006-82-4], tert-butyl peroxyisobutyrate, tert-butyl peroxypivalate, 2,5-dimethyl-2,5-bis(benzoylperoxy)hexane [CAS 618-77-1], tert-butyl peroxy(2-ethylbutyrate), 2,5-dimethyl-2,5-bis(2-ethylhexanoylperoxy)-hexane [CAS 13052-09-0], di-tert-butyl diperoxyazelate [CAS 16580-06-6], tert-amyl peroxy(2-ethylhexanoate) [CAS 686-31-7], di-tert-butyldiperoxyphthalate, O,O-tert-butyl hydrogen monoperoxymaleate, dimethyl peroxyoxalate, di-tert-butyl diperoxyoxalate, and tert-butyl peroxyneodecanoate [CAS 748-41-4].

Peroxycarbonates, exemplified by tert-butylperoxy isopropyl carbonate.

Peroxydicarbonates, exemplified by diisopropyl peroxydicarbonate [CAS 105-64-6], di-sec-butyl peroxydicarbonate, di-n-propyl peroxydicarbonate [CAS 16066-38-9], di(2-ethylhexyl) peroxydicarbonate, dicyclohexyl peroxydicarbonate [CAS 1561-49-5], and dicetyl peroxydicarbonate [CAS 26322-14-5].

Another class of suitable organic free radical initiators comprises the organic azo-nitrile initiators, of which there are many. Examples of suitable azo-nitrile initiators include 2,2'-azobis(2-methylpropanenitrile) [CAS 78-67-1], 2,2'-azobis(2-methylbutanenitrile) [CAS 13472-08-7], 2,2'-azobis(2,4-dimethylpentanenitrile) [CAS 4419-11-8], 2,2'-azobis(4-methoxy-2,4-dimethylpentanenitrile) [CAS 15545-97-8], 1,1'-azobis(cyclohexanecarbonitrile) [CAS 2094-98-6], 4,4'-azobis(4-cyanopentanoic acid) [CAS 2638-94-0], 2,2'-azobis(2-methylpentanenitrile), 2,2'-azobis(2,3-dimethylbutanenitrile), 2,2'-azobis(2-methylhexanenitrile), 2,2'-azobis(2,3-dimethylpentanenitrile), 2,2'-azobis(2,3,3-trimethylbutanenitrile), 2,2'-azobis(2,4,4-trimethylpentanenitrile), 2,2'-azobis(2-methyl-3-phenylpropanenitrile), 2,2'-azobis(2-cyclohexylpropanenitrile), 1,1'-azobis(cycloheptanecarbonitrile), 1,1'-azobis(cyclooctanecarbonitrile), 1,1'-azobis(cyclodecanecarbonitrile), 2-(tert-butylazo)-4-methoxy-2,4-dimethylpentanenitrile [CAS 55912-17-9], 2-(tert-butylazo)-2,4-dimethylpentanenitrile [CAS 55912-18-0], 2-(tert-butylazo)-2-methylpropanenitrile [CAS 25149-46-6], 2-(tert-butylazo)-2-methylbutanenitrile [CAS 52235-20-8], 1-(tert-amylazo)cyclohexanecarbonitrile [CAS 55912-19-1], 1-(tert-butylazo)cyclohexanecarbonitrile [CAS 25149-47-7], and 2-[(1-chloro-1-phenylethyl)azo]-2-phenylpropanenitrile.

It is believed that many inorganic free radical initiators and metallic organic free-radical initiators are suitable for use in the present invention. Examples of inorganic free radical initiators include sodium peroxide [CAS 1313-60-6], lithium peroxide [CAS 12031-80-0], potassium peroxide [17014-71-0], magnesium peroxide [CAS 14452-57-4], calcium peroxide [CAS 1305-79-9], strontium peroxide [CAS 1314-18-7], barium peroxide [1304-29-6], the sodium peroxyborates, sodium carbonate sesqui(peroxyhydrate) [CAS 15630-89-4], disodium peroxydicarbonate [CAS 3313-92-6], dipotassium peroxydicarbonate [CAS 589-97-9], monosodium peroxymonocarbonate [CAS 20745-24-8], monopotassium peroxymonocarbonate [CAS 19024-61-4], peroxymonophosphoric acid [CAS 13598-52-2], peroxydiphosphoric acid [CAS 13825-81-5], tetrapotassium peroxydiphosphate [CAS 15593-49-4], tetra sodium pyrophosphate bis(peroxyhydrate) [CAS 15039-07-3], peroxymonosulfuric acid [CAS 7722-86-3], oxone peroxymonosulfate [CAS 37222-66-5], peroxydisulfuric acid [CAS 13445-49-3], diammonium peroxydisulfate [CAS 7727-54-0], dipotassium peroxydisulfate [CAS 7727-21-1], disodium peroxydisulfate [CAS 7775-27-1], and zinc peroxide [1314-22-3]. Examples of metallic organic free radical initiators include diethyloxyaluminum tert-cumyl peroxide [CAS 34914-67-5], tri-tert-butyl perborate [CAS 22632-09-3], tert-butyl triethylgermanium peroxide [CAS 26452-74-4], dioxybis[triethylgermane] [CAS 58468-05-6], (tert-butyldioxy)-triethylplumbane [CAS 18954-12-6], OO-tert-butyl dimethyl phosphorperoxoate [CAS 18963-64-9], tetrakis(tert-butyl) peroxysilicate [CAS 10196-46-0], dioxybis[trimethylsilane] [CAS 5796-98-5], (tert-butyldioxy)-trimethylsilane [CAS 3965-63-7], dioxybis[triethylstannane] [CAS 4403-63-8], and (tert-butyldioxy)trimethylstannane [CAS 20121-56-6]. Other examples are given in *Kirk-Othmer Encyclopedia of Chemical Technology*, third edition, volume 17, pages 2–22, 34, 49–50, 54–55, and 59 (1982), the disclosure of which is, in its entirety, incorporated herein by reference.

The amount of free radical initiator present in the liquid phase during the reaction is susceptible to very wide variation. In general, the free radical initiator should be present in sufficient amount to promote the isomerization reaction. The minimum and maximum amounts are not limited by any theory, but by practical convenience. Since initiator deactivation is believed to proceed in at least some degree as the isomerization progresses and since it is difficult to ascertain how much active free radical initiator is present at any given instant, the relative proportions of free radical initiator and 1,2-dichloroethene (both stereoisomers) are best expressed in terms of the weight ratios of these materials introduced to the reaction, although it should be recognized that the amount of active free radical initiator present in the liquid phase is probably less at most times. If initiator deactivation is significant, the addition of free radical initiator may be made intermittently or continuously to remedy the problem. In most cases, the free radical initiator and the 1,2-dichloroethene are combined at a weight ratio of the free radical initiator to the 1,2-dichloroethene in the range of from about 5 parts per million parts (ppm) to about 5000 ppm. Often the weight ratio is in the range of from about 5 ppm to about 2000 ppm. Frequently, the weight ratio is in the range of from about 20 ppm to about 1500 ppm. From about 50 ppm to about 1000 ppm is preferred.

The liquid reaction mixture in which the isomerization reaction is conducted may contain only 1,2-dichloroethene and free radical initiator or it may also contain other materials which do not seriously interfere with the isomerization reaction. In its broadest aspects, the 1,2-dichloroethene should be present in more than a trivial or inconsequential amount. Usually the 1,2-dichloroethene constitutes at least about 2 weight percent of the reaction mixture, taken on an initiator-free basis. Frequently the 1,2-dichloroethene constitutes at least about 10 weight percent of the reaction mixture, taken on an initiator-free basis. In many cases the 1,2-dichloroethene constitutes at least about 50 weight percent of the reaction mixture, taken on an initiator-free basis. Often the 1,2-dichloroethene constitutes at least about 70 weight percent of the reaction mixture taken on an initiator-free basis. At least about 95 weight percent, taken on an initiator-free basis, is preferred.

The reaction may be conducted batchwise, semi-batchwise, continuously, or semi-continuously.

The temperature of the reaction may vary considerably. Usually, however, the temperature is in the range of from about 0° C. to about 150° C. In many cases the temperature is in the range of from about 0° C. to about 100° C. Often the temperature is in the range of from about 35° C. to about 70° C. From about 45° C. to about 60° C. is preferred.

The isomerization reaction is conveniently, but not necessarily, conducted at reflux temperature.

As a matter of convenience, the isomerization reaction is usually conducted at about ambient atmospheric pressure or slightly above, although greater or lesser pressures may be used as desired. When the reaction is conducted at reflux, the reflux temperature may be altered from the atmospheric reflux temperature by employing pressures above or below ambient atmospheric pressure.

When desired, the reaction mixture may be distilled to separate the trans-1,2-dichloroethene from the cis-1,2-dichloroethene. This may be accomplished after the isomerization reaction has been completed or while the isomerization reaction is being conducted. In the latter instance the desired stereoisomer may be recovered while the other stereoisomer is returned to the reaction mixture for isomerization. By operating in this manner, the concentrations of the stereoisomers are prevented from approaching the equilibrium concentrations too closely thereby enhancing the overall rate of reaction and permitting essentially all of the undesired stereoisomer to be converted to the desired stereoisomer.

The invention is further described in conjunction with the following examples which are to be considered illustrative rather than limiting, and in which all parts are by weight and all percentages are percentages by weight unless otherwise specified.

EXAMPLE I

Various materials were evaluated as catalysts for the isomerization of cis-1,2-dichloroethene to trans-1,2-dichloroethene using organic feedstock having the composition shown in Table 1. To this end, 200 milliliters (276 grams) of the organic feedstock was placed in each of seven 300 milliliter round bottom flasks. Several boiling chips were added to six of the flasks. A different material to be evaluated was added to six of the flasks. The identities of the materials and their amounts are shown in Table 2. Each flask was fitted with a reflux condenser cooled by an ethylene glycol-water mixture from a constant temperature bath controlled at 8° C. Each flask was heated with an electric heating mantle controlled by a variable autotransformer. The samples were refluxed for about 17½ hours and then analyzed. The analytical results are shown in Table 3.

TABLE 1

| Organic Feedstock | |
|---|---|
| Component | Concentration, wt. percent |
| trans-1,2-Dichloroethene | 3.87 |
| cis-1,2-Dichloroethene | 54.32 |
| Vinylidene Chloride | 0.12 |
| Chloroform | 4.85 |
| Carbon Tetrachloride | 34.52 |
| Trichloroethene | 2.32 |

TABLE 2

| Materials Evaluated | | |
|---|---|---|
| Flask No. | Material | Amount, grams |
| 1 | None (Control) | — |
| 2 | Water | 5 |
| 3 | 2,2'-Azobis (2-methylpropanenitrile) | 0.26 |
| 4 | Dibenzoyl Peroxide | 0.28 |
| 5 | Anhydrous Ferric Chloride | 0.32 |
| 6 | Aliquat #336 Methyltrioctylammonium chloride [CAS 5137-55-3] | 0.41 |
| 7 | Trioctylamine [CAS 1116-76-3] | 0.35 |

TABLE 3

| Reaction Product Analyses, wt. percent | | | | | | | |
|---|---|---|---|---|---|---|---|
| | Flask Number | | | | | | |
| Component | 1 | 2 | 3 | 4 | 5 | 6 | 7 |
| trans-1,2-Dichloroethene | 3.82 | 3.78 | 17.34 | 18.06 | 3.87 | 3.68 | 3.82 |
| cis-1,2-Dichloroethene | 54.30 | 54.25 | 41.12 | 40.09 | 54.34 | 54.30 | 54.25 |
| Vinylidene Chloride | 0.08 | 0.04 | 0.07 | 0.07 | 0.02 | 0.08 | 0.08 |
| Chloroform | 4.85 | 4.93 | 4.78 | 4.93 | 4.88 | 4.85 | 4.83 |
| Carbon Tetrachloride | 34.60 | 34.68 | 34.45 | 34.62 | 34.59 | 34.60 | 34.55 |
| Trichloroethene | 2.35 | 2.32 | 2.24 | 2.23 | 2.30 | 2.49 | 2.47 |

The data show that cis-1,2-dichloroethene is isomerized to trans-1,2-dichloroethene at reflux temperatures in the presence of the free radical initiators 2,2'-azobis(2-methylpropanenitrile) (Flask No. 3) and dibenzoyl peroxide (Flask No. 4). The materials evaluated in Flasks No. 2, 5, 6, and 7 are not free radical initiators and were not effective in promoting the isomerization.

EXAMPLE II

A 12 liter boiling flask equipped with a reflux condenser was charged with 10.5 kilograms of distilled high purity trans-1,2-di-chloroethene and 4.5 grams of 2,2'-azobis(2-methylpropanenitrile). Cooling water was provided to the reflux condenser from a refrigerated bath controlled at 4° C. The flask was heated and the charged materials were refluxed for 30 hours. At the conclusion of this period heating was discontinued and the reaction mixture was allowed to cool. Gas chromatographic analysis showed the reaction mixture to contain 81.08 weight percent cis-1,2-dichloroethene and 18.02 weight percent trans-1,2-dichloroethene. These data show that trans-1,2-dichloroethene is isomerized to cis-1,2-dichloroethene at reflux temperatures in the presence of 2,2'-azobis(2-methylpropanenitrile).

EXAMPLE III

In a series of batch reactions, cis-1,2-dichloroethene was isomerized to trans-1,2-dichloroethene. For each batch, approximately 16 to 18 liters of feedstock was charged to a 22 liter distillation pot. The feedstock composition for each batch was within the ranges shown in Table 4.

TABLE 4

| Feedstock Composition | |
|---|---|
| Component | Composition, wt. percent |
| trans-1,2-Dichloroethene | 2–5 |
| cis-1,2-Dichloroethene | 50–55 |
| Chloroform | 6–8 |
| Carbon Tetrachloride | 32–42 |

To the charged feedstock was added from 25 to 35 grams of either 2,2'-azobis(2-methylpropanenitrile) or dibenzoyl peroxide. The distillation pot was fitted with a 5.08 centimeter diameter vacuum jacketed Oldershaw distillation column containing 40 trays. The charged material was heated to boiling and refluxed for approximately 3 hours. Then an overhead stream was collected at a rate of approximately 4 cubic centimeters/minute. The composition of this overhead stream was from 40 to 70 weight percent trans-dichloroethene. Distillation and collection of the overhead stream was continued until the cis-1,2-dichloroethene content of the material remaining in the distillation pot was about 10 weight percent. The overhead material which had been collected was then distilled to yield a product with an assay of greater than 95 weight percent trans-1,2-dichloroethene.

EXAMPLE IV

A distillation column having 60 trays was configured so that feed was introduced on the eighth tray from the bottom. The distillation column was equipped with a steam-heated thermosyphon reboiler and a water-cooled overhead condenser. Bottoms material was pumped to a tee. One branch of the tee was connected to a valve which was connected to the inlet of a small tank. The lid of the tank was equipped with an inlet for nitrogen gas and was held in place with flange bolts. The outlet from the tank was connected to the column such that liquid from the tank would be introduced on the tenth tray from the bottom. Bottoms product was removed continuously through the other branch of the tee and forwarded to suitable storage containers. Condensate from the condenser was forwarded to a reflux drum. Liquid from the reflux drum was divided into two streams: one stream was returned to the top of the column as reflux while the other stream was continuously forwarded as overhead product to suitable storage containers.

The column was operated in continuous fashion with a pressure of about 82.7 kilopascals, gauge, at the top of the column, a bottoms temperature of about 87.8° C., and a reflux of about 378.5 liters/minute. The feed was at a temperature of about 73.3° C. when introduced to the column. Every two hours the small tank was purged with nitrogen, the lid was removed, 2.268 kilograms of 2,2'-azobis(2-methylpropanenitrile) was added to the tank, the lid was installed, the tank was purged with nitrogen, and the 2,2'-azobis(2-methylpropanenitrile) was flushed from the tank into the column with bottoms liquid which was allowed to flow through the tank for a few minutes. The 2,2'-azobis(2-methylpropanenitrile) went to the bottom of the column and the reboiler with the high liquid traffic in the column. The flow rates and gas chromatographic analyses of the feed, overhead product, and bottoms product are shown in Table 5.

TABLE 5

| Component | Flow Rates and Compositions | | | | | |
|---|---|---|---|---|---|---|
| | Feed | | Bottoms Product | | Overhead Product | |
| | wt % | kg/min | wt % | kg/min | wt % | kg/min |
| trans-1,2-Dichloroethene | 12.38 | 2.359 | 0.05 | 0.005 | 99.92 | 9.553 |
| cis-1,2-Dichloroethene | 39.60 | 7.543 | 3.61 | 0.345 | 0.07 | 0.005 |
| Carbon Tetrachloride | 36.94 | 7.035 | 79.84 | 7.575 | 0.00 | 0.000 |

TABLE 5-continued

| Component | Flow Rates and Compositions | | | | | |
|---|---|---|---|---|---|---|
| | Feed | | Bottoms Product | | Overhead Product | |
| | wt % | kg/min | wt % | kg/min | wt % | kg/min |
| Other Components | 11.08 | 2.109 | 16.50 | 1.565 | 0.01 | 0.000 |

The data show that more than 95.3 percent of the cis-1,2-dichloroethene fed to the column was converted to trans-1,2-dichloroethene. The material balance for the 1,2-dichloroethene (both isomers) was good. The material balance for the carbon tetrachloride and the other components taken together was also good. The data do tend to suggest, however, that compounds were converted to carbon tetrachloride. Whether this is the case or whether the difference is due to analytical error remains to be established.

It is believed that removal of the trans-1,2-dichloroethene from the bottoms kept the ratio of the cis-isomer to the trans-isomer in the bottoms liquid favorable for continued conversion.

EXAMPLE V

A Paar pressure reactor equipped with a stirrer and a dip tube for sampling was used to convert cis-1,2-dichloroethene to trans-1,2-dichloroethene using organic feedstock having the composition shown in Table 6.

TABLE 6

| Organic Feedstock | |
|---|---|
| Component | Concentration, wt. percent |
| trans-1,2-Dichloroethene | 6.34 |
| cis-1,2-Dichloroethene | 82.47 |
| Vinylidene Chloride | 0.004 |
| Chloroform | 3.53 |
| Carbon Tetrachloride | 7.37 |
| Other Components | 0.286 |

A coil was formed from thick walled stainless steel tubing having an outside diameter of 6.35 millimeters and a length of 73.66 centimeters. The calculated volume of the coil was 13 cubic centimeters. A solution of 0.10 gram of 2,2'-azobis(2-methylpropanenitrile) dissolved in about 10 cubic centimeters of the organic feedstock was placed in the coil. One end of the coil was attached to an entry port of the reactor. The other end of the coil was attached to a valve which was connected to a nitrogen gas system regulated at a pressure of about 827 kilopascals, gauge. The reactor was cleaned, dried, and charged with 400 cubic centimeters (515 grams) of the organic feedstock. The reactor was then sealed and heating by an electric heater controlled with a thermostat was begun. A thermocouple was used for measurement of reactor temperatures. Temperatures and pressures at various times after heating was initially begun are shown in Table 7.

TABLE 7

| Conditions During Heating | | |
|---|---|---|
| Time, minutes | Temperature, °C. | Pressure, kPa, gauge |
| 0 | 25 | 0 |
| 10 | 31 | 0 |
| 15 | 56 | 41 |
| 20 | 85 | 152 |
| 25 | 112 | 303 |
| 30 | 116 | 345 |
| 35 | 120 | 400 |

TABLE 7-continued

| Time, minutes | Conditions During Heating | |
|---|---|---|
| | Temperature, °C. | Pressure, kPa, gauge |
| 37 | 123 | 427 |
| 42 | 126 | 476 |
| 47 | 127 | 476 |
| 50 | 125 | 455 |
| 53 | 124 | 455 |
| 57 | 124 | 455 |

Since the reactor at this time had maintained the desired temperature of 125°±2° C. for at least 20 minutes, the solution of 2,2'-azobis(2-methylpropanenitrile) in the coil was blown into the reactor using nitrogen gas and sampling was begun. The reactor conditions and composition of the liquid reaction mixture at various times after the introduction of free-radical initiator are shown in Table 8.

TABLE 8

Reactor Conditions and Analytical Results

| Time, minutes:seconds | Temperature, °C. | Pressure, kPa | Concentration, wt percent | |
|---|---|---|---|---|
| | | | trans-DCE | cis-DCE |
| 0:00 | 124 | 455 | 6.34 | 82.47 |
| 0:20 | | | 12.14 | 76.52 |
| 0:40 | | | 20.31 | 68.13 |
| 1:00 | | | 22.66 | 65.84 |
| 1:20 | | | 22.68 | 65.79 |
| 1:40 | | | 23.07 | 64.14 |
| 8:00 | 125 | 510 | 22.38 | 65.87 |
| 15:00 | 126 | 524 | 22.49 | 65.36 |
| 33:00 | 126 | 531 | 23.26 | 65.12 |

Although the present invention has been described with reference to specific details of certain embodiments thereof, it is not intended that such details should be regarded as limitations upon the scope of the invention except insofar as they are included in the accompanying claims.

We claim:

1. A method comprising isomerizing one stereoisomer of 1,2-dichloroethene to the other stereoisomer of 1,2-dichloroethene in the liquid phase and in the presence of organic free radical initiator.

2. The method of claim 1 wherein the isomerization is conducted at temperatures in the range of from about 0° C. to about 150° C.

3. The method of claim 1 wherein the isomerization is conducted at temperatures in the range of from about 0° C. to about 100° C.

4. The method of claim 1 wherein the isomerization is conducted at temperatures in the range of from about 35° C. to about 70° C.

5. The method of claim 1 wherein the isomerization is conducted under reflux conditions.

6. The method of claim 1 wherein said free radical initiator and 1,2-dichloroethene are combined at a weight ratio of said free radical initiator to said 1,2-dichloroethene in the range of from about 5 ppm to about 5000 ppm.

7. The method of claim 1 wherein said free radical initiator and 1,2-dichloroethene are combined at a weight ratio of said free radical initiator to said 1,2-dichloroethene in the range of from about 5 ppm to about 2000 ppm.

8. The method of claim 1 wherein 1,2-dichloroethene constitutes at least about 2 weight percent of the reaction mixture, taken on an initiator-free basis.

9. The method of claim 1 wherein 1,2-dichloroethene constitutes at least about 10 weight percent of the reaction mixture, taken on an initiator-free basis.

10. The method of claim 1 wherein the free radical initiator is organic peroxygen-containing free radical initiator.

11. The method of claim 1 wherein the free radical initiator is dibenzoyl peroxide.

12. The method of claim 1 wherein the free radical initiator is organic azo-nitrile free radical initiator.

13. The method of claim 1 wherein the free radical initiator is 2,2'-azobis(2-methylpropanenitrile).

14. The method of claim 1 wherein cis-1,2-dichloroethene is isomerized to trans-1,2-dichloroethene in the liquid phase and in the presence of organic free radical initiator.

15. The method of claim 14 wherein the isomerization is conducted at temperatures in the range of from about 0° C. to about 150° C.

16. The method of claim 14 wherein the isomerization is conducted at temperatures in the range of from about 0° C. to about 100° C.

17. The method of claim 14 wherein the isomerization is conducted at temperatures in the range of from about 35° C. to about 70° C.

18. The method of claim 14 wherein the isomerization is conducted under reflux conditions.

19. The method of claim 14 wherein said free radical initiator and 1,2-dichloroethene are combined at a weight ratio of said free radical initiator to said 1,2-dichloroethene in the range of from about 5 ppm to about 5000 ppm.

20. The method of claim 14 wherein said free radical initiator and 1,2-dichloroethene are combined at a weight ratio of said free radical initiator to said 1,2-dichloroethene in the range of from about 5 ppm to about 2000 ppm.

21. The method of claim 14 wherein 1,2-dichloroethene constitutes at least about 2 weight percent of the reaction mixture, taken on an initiator-free basis.

22. The method of claim 14 wherein 1,2-dichloroethene constitutes at least about 10 weight percent of the reaction mixture, taken on an initiator-free basis.

23. The method of claim 14 wherein the free radical initiator is organic peroxygen-containing free radical initiator.

24. The method of claim 14 wherein the free radical initiator is dibenzoyl peroxide.

25. The method of claim 14 wherein the free radical initiator is organic azo-nitrile free radical initiator.

26. The method of claim 14 wherein the free radical initiator is 2,2'-azobis(2-methylpropanenitrile).

27. The method of claim 1 wherein trans-1,2-dichloroethene is isomerized to cis-1,2-dichloroethene in the liquid phase and in the presence of organic free radical initiator.

28. The method of claim 27 wherein the isomerization is conducted at temperatures in the range of from about 0° C. to about 150° C.

29. The method of claim 27 wherein the isomerization is conducted at temperatures in the range of from about 0° C. to about 100° C.

30. The method of claim 27 wherein the isomerization is conducted at temperatures in the range of from about 35° C. to about 70° C.

31. The method of claim 27 wherein the isomerization is conducted under reflux conditions.

32. The method of claim 27 wherein said free radical initiator and 1,2-dichloroethene are combined at a weight ratio of said free radical initiator to said 1,2-dichloroethene in the range of from about 5 ppm to about 5000 ppm.

33. The method of claim 27 wherein said free radical initiator and 1,2-dichloroethene are combined at a weight ratio of said free radical initiator to said 1,2-dichloroethene in the range of from about 5 ppm to about 2000 ppm.

34. The method of claim 27 wherein 1,2-dichloroethene constitutes at least about 2 weight percent of the reaction mixture, taken on an initiator-free basis.

35. The method of claim 27 wherein 1,2-dichloroethene constitutes at least about 10 weight percent of the reaction mixture, taken on an initiator-free basis.

36. The method of claim 27 wherein the free radical initiator is organic peroxygen-containing free radical initiator.

37. The method of claim 27 wherein the free radical initiator is benzoyl peroxide.

38. The method of claim 27 wherein the free radical initiator is organic azo-nitrile free radical initiator.

39. The method of claim 27 wherein the free radical initiator is 2,2'-azobis(2-methylpropanenitrile).

40. A method of comprising isomerizing 1,2-cis-dichloroethene to trans-1,2-dichloroethene in the liquid phase and in the presence of 2,2'-azobis(2-methylpropanenitrile) wherein the isomerization is conducted under relux conditions at temperatures in the range of from about 35° C. to about 70° C.

41. A method comprising isomerizing trans-1,2-dichloroethene to cis-1,2-dichloroethene in the liquid phase and in the presence of 2,2'-azobis(2-methylpropanenitrile) wherein the isomerization is conducted under relux conditions at temperatures in the range of from about 35° C. to about 70° C.

42. A method comprising isomerizing one stereoisomer of 1,2-dichloroethene to the other stereoisomer of 1,2-dichloroethene in the liquid phase and in the presence of free radical initiator.

43. The method of claim 42 wherein the isomerization is conducted at temperatures in the range of from about 0° C. to about 150° C.

44. The method of claim 42 wherein the isomerization is conducted under reflux conditions.

45. The method of claim 42 wherein said free radical initiator and 1,2-dichloroethene are combined at a weight ratio of said free radical initiator to said 1,2-dichloroethene in the range of from about 5 ppm to about 5000 ppm.

46. The method of claim 42 wherein 1,2-dichloroethene constitutes at least about 2 weight percent of the reaction mixture, taken on an initiator-free basis.

47. The method of claim 42 wherein cis-1,2-dichloroethene is isomerized to trans-1,2-dichloroethene in the liquid phase and in the presence of free radical initiator.

48. The method of claim 47 wherein the isomerization is conducted at temperatures in the range of from about 0° C. to about 150° C.

49. The method of claim 47 wherein the isomerization is conducted under reflux conditions.

50. The method of claim 47 wherein said free radical initiator and 1,2-dichloroethene are combined at a weight ratio of said free radical initiator to said 1,2-dichloroethene in the range of from about 5 ppm to about 5000 ppm.

51. The method of claim 47 wherein 1,2-dichloroethene constitutes at least about 2 weight percent of the reaction mixture, taken on an initiator-free basis.

52. The method of claim 42 wherein trans-1,2-dichloroethene is isomerized to cis-1,2-dichloroethene in the liquid phase and in the presence of free radical initiator.

53. The method of claim 52 wherein the isomerization is conducted at temperatures in the range of from about 0° C. to about 150° C.

54. The method of claim 52 wherein the isomerization is conducted under reflux conditions.

55. The method of claim 52 wherein said free radical initiator and 1,2-dichloroethene are combined at a weight ratio of said free radical initiator to said 1,2-dichloroethene in the range of from about 5 ppm to about 5000 ppm.

56. The method of claim 52 wherein 1,2-dichloroethene constitutes at least about 2 weight percent of the reaction mixture, taken on an initiator-free basis.

* * * * *